United States Patent
Lürssen

[11] 3,972,705
[45] Aug. 3, 1976

[54] AMIDOTHIONOPHOSPHONIC ACID ESTER CONTAINING PLANT GROWTH REGULANTS

[75] Inventor: Klaus Lürssen, Gross-Koenigsdorf, Germany

[73] Assignee: Bayer Aktiengesellschaft, Leverkusen, Germany

[22] Filed: Dec. 23, 1974

[21] Appl. No.: 535,901

[30] Foreign Application Priority Data
Jan. 16, 1974 Germany............................ 2401881

[52] U.S. Cl........................................ 71/78; 71/87
[51] Int. Cl.². ............................................ A01N 9/36
[58] Field of Search................................... 71/87, 78

[56] References Cited
UNITED STATES PATENTS

| | | | |
|---|---|---|---|
| 3,644,600 | 2/1972 | Beriger et al. ....................... | 71/87 X |
| 3,819,754 | 6/1974 | Aya et al. ............................ | 71/87 X |
| 3,823,004 | 6/1974 | Schrader et al..................... | 71/87 X |

*Primary Examiner*—Lewis Gotts
*Assistant Examiner*—Catherine L. Mills
*Attorney, Agent, or Firm*—Burgess, Dinklage & Sprung

[57] ABSTRACT

Methods for regulating the growth of plants comprising applying to the plants or their habitat an amidothionophosphonic acid ester compound of the formula:

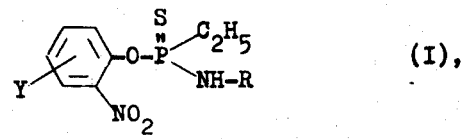

(I), wherein
R is alkyl of up to 6 carbon atoms or cycloalkyl; and
Y is hydrogen, halogen or alkyl of from 1 to 6 carbon atoms.

1 Claim, No Drawings

AMIDOTHIONOPHOSPHONIC ACID ESTER CONTAINING PLANT GROWTH REGULANTS

The present invention relates to the use, as agents for regulating plant growth, of certain amidothionophosphonic acid esters, which are known as herbicides.

It is known that maleic acid hydrazide can be employed for inhibiting plant growth and for suppressing the growth of side shoots in tobacco plants (see U.S. Pat. Nos. 2,575,954; 2,614,916 and 2,805,926, British Patent Specification 672,596 and Can. J. Biol. 31, 426 (1953)). The mode of action of this compound is however not always entirely satisfactory, especially if fairly low amounts and concentrations are used.

It has now been found that the amidothionophosphonic acid esters of the general formula

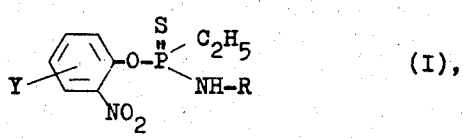

in which
R is lower alkyl or cycloalkyl, and
Y is hydrogen, halogen or lower alkyl,
are distinguished by a very good plant-growth-regulating activity.

The present invention thus provides a method of regulating the growth of plants, which comprises applying to the plants, or to a plant habitat, a compound of the formula (I) above alone or in admixture with a diluent or carrier.

Preferably, R is straight-chain or branched alkyl of from 1 to 6 carbon atoms, especially methyl, ethyl, n-propyl, isopropyl, n-butyl, isobutyl, sec.-butyl or tert.-butyl, or cycloalkyl of from 3 to 8 carbon atoms, especially cyclopentyl and cyclohexyl, and Y is hydrogen, fluorine, chlorine, bromine, iodine or straight-chain or branched alkyl of from 1 to 6 carbon atoms, especially methyl, ethyl, propyl or tert.-butyl.

Surprisingly, the amidothionophosphonic acid esters which can be used according to the invention show a substantially stronger growth-regulating activity than maleic acid hydrazide, known from the state of the art, which is the nearest active compound of the same type of action. The compounds which can be used according to the invention thus represent a valuable enrichment of the art.

The following may be mentioned as examples of the compounds which can be used according to the invention: O-(2-nitro-4-methylphenyl)-N-isopropyl-ethanethionophosphonamide, O-(2-nitrophenyl)-N-methyl-ethanethionophosphonamide, O-(2-nitro-4-methylphenyl)-N-methyl-ethanethionophosphonamide, O-(2-nitro-4-methylphenyl)-N-ethyl-ethanethionophosphonamide, O-(2-nitrophenyl)-N-n-propyl-ethanethionophosphonamide, O-(2-nitrophenyl)-N-isopropryl-ethanethionophosphonamide, O-(2-nitro-4-methylphenyl)-N-n-butyl-ethanethionophosphonamide, O-(2-nitro-4-methylphenyl)-N-isobutyl-ethanethionophosphonamide, O-(2-nitrophenyl)-N-sec.-butyl-ethanethionophosphonamide, O-(2-nitro-4-methylphenyl)-N-sec.-butyl-ethanethionophosphonamide, O-(2-nitrophenyl)-N-cyclohexyl-ethane-thionophosphonamide, O-(2-nitro-4-tert.-butylphenyl)-N-isopropylethanethionophosphonamide, O-(2-nitro-4-chlorophenyl)-N-isopropyl-ethanethionophosphonamide and O-(2-nitro-4-bromophenyl)-N-isopropyl-ethanethionophosphonamide.

The amidothionophosphonic acid esters which can be used according to the invention have been described in the literature and are known to possess herbicidal properties (see German Offenlegungsschrift (German Published Specification) 2,156,447). However, their use for regulating plant growth is new.

The amidothionophosphonic acid esters can be prepared, for example, by reacting ethanethionophosphonamide chlorides with substituted phenols or their alkali metal salts in the presence of inert solvents and optionally in the presence of acid-binding agents at temperatures of between 0°C and 100°C. The reaction products are isolated in accordance with the customary methods, for example by concentrating the reaction mixture, taking up the residue in a suitable solvent, extracting this solution with water, then drying it over sodium sulphate and evaporating it, and either recrystallizing the residue or subjecting it to a fractional vacuum distillation.

The amidothionophosphonic acid esters can also be prepared by reacting ethanethionophosphonyl chlorides with primary amines in the presence of inert solvents at temperatures of between 0°C and 100°C. The reaction products are isolated in the usual manner by washing the reaction mixture successively with weakly acid water, weakly alkaline water and pure water, then drying the organic phase over sodium sulphate and subsequently concentrating it, and either recrystallizing the residue or subjecting it to a fractional vacuum distillation.

The active compounds which can be used according to the invention intervene in the physiological process of plant growth and can therefore be used as plant-growth regulators.

The diverse effects of the active compounds depend essentially on the time at which they are used, in relation to the stage of development of the seed or of the plant, and on the concentrations used.

Plant-growth regulators are used for various purposes related to the stage of development of the plant.

The growth of the plants can be strongly inhibited by means of the compounds which can be used according to the invention. This inhibition of growth is of interest in the case of grasses, so as to reduce the frequency of cutting the grass. Inhibition of vegetative growth is also very important in cereals since lodging can thereby be reduced or completely prevented.

In the case of many crop plants, inhibition of vegetative growth permits denser planting of the crop so that an increased yield relative to the soil area can be achieved. A further mechanism of increasing the yield by means of growth inhibitors is based on the fact that the nutrients benefit blossoming and fruit formation to an increased extent while vegetative growth is restricted.

The growth regulators can also be used to increase the vegetative growth. This is of great value if the vegetative parts of the plants are harvested. A promotion of vegetative growth can however also simultaneously lead to a promotion of generative growth so that, for example, more fruit, or larger fruit, is formed.

Parthenocarpous fruit can be formed under the influence of growth regulators. Furthermore, the gender of the flowers can be influenced.

Using growth regulators, it is also possible to influence favorably the production or efflux of secondary plant materials. The stimulation of the latex flow in rubber trees may be mentioned as an example.

During the growth of the plant, lateral branching can also be increased by chemical breaking of the apical dominance. There is interest in this, for example, in the case of plant propagation by cuttings. However, depending on the concentration, it is also possible to inhibit the growth of side shoots in tobacco plants after decapitation and thus to promote leaf growth.

The influence of growth regulators on the number of leaves on plants can be so controlled as to achieve defoliation, for example to facilitate harvesting or to lower the transpiration at a point in time at which the plant is to be transplanted.

Under certain conditions, premature shedding of fruit can be prevented or shedding of fruit assisted, in the sense of a chemical thinning-out, up to a certain degree. However, assisting the shedding of fruit can also be utilized by carrying out the treatment at harvest time, which facilitates harvesting.

Using growth regulators it is furthermore possible to accelerate or delay ripening of fruit and improve the coloring of fruit. Concentrating the ripening of fruit within a certain period of time is also possible. The desired effects can be achieved by varying the concentrations of active compounds used and by application at various times during the development of the plant.

Using growth regulators, frost resistance and drought resistance can be induced in plants.

The latent period of seeds or buds of plants, that is to say the endogenic annual rhythm, can be influenced by growth regulators so that the plants, for example, germinate, shoot or blossom at a time at which they normally show no readiness to do so.

Using growth regulators it is also possible to delay the shooting of buds or the germination of seeds, for example to avoid damage by late frosts in regions where frost is a hazard.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulphoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulphonates, alkyl sulphates and aryl sulphonates as well as albumin hydrolyzation products; and preferred examples of dispersing agents include lignin sulphite waste liquors and methyl cellulose.

The active compounds which can be used according to the invention can be present in the formulations as a mixture with other active compounds.

The formulations in general contain from 0.1 to 95 percent by weight of active compound, preferably from 0.5 to 90 percent by weight.

The active compounds can be used as such, in the form of their formulations or in the use forms prepared therefrom, such as ready-to-use solutions, emulsifiable concentrates, emulsions, foams, suspensions, wettable powders, pastes, soluble powders, dusting agents and granules. They may be used in the customary manner, for example, by watering, spraying, atomizing, scattering, dusting and the like.

The active-compound concentrations can be varied within a fairly wide range. In general, concentrations of 0.0005 to 2%, preferably of 0.01 to 0.5%, by weight, are used.

Furthermore, 0.1 to 100 kg, preferably 1 to 10 kg, of active compound are in general employed per hectare of ground.

The preferred period of time within which the growth regulators are used depends on the climatic and vegetative circumstances.

The present invention further provides methods of yielding plants the growth of which has been regulated by their being grown in areas in which immediately prior to and/or during the time of the growing a compound of the formula (I) above was applied alone or in admixture with a diluent or carrier.

The examples which follow show the activity of the compounds which can be used according to the invention as growth regulators, without thereby excluding the possibility of further applications as growth regulators.

EXAMPLE A

Suppression of side shoot growth in tobacco

Solvent: 10 parts by weight of methanol
Emulsifier: 2 parts by weight of polyethylene-sorbitan monolaurate To produce a suitable preparation of active compound, 1 part by weight of active compound was mixed with the stated amounts of solvent and emulsifier and made up to the desired concentration with water.

The apical meristems of 30 cm high tobacco plants were cut out one da before the plants were treated with the preparation of active compound, in order to stimulate the shooting of the leaf axle buds. The plants were each sprayed with 20 ml of an active compound preparation of a certain concentration. After one month, the damage was rated and the side shoots were broken off and weighed. The weight of the side shoots served as a measure of branching.

The degree of damage to the plants was designated in terms of the numbers 0 – 5, which have the following meaning:
0—no damage
1—some slight scorching spots
2—distinct damage to leaves
3—some leaves and parts of stems partially dead
4—plant partially destroyed
5—plant completely dead The active compounds, active-compound concentrations and results can be seen from the table which follows:

To produce a suitable preparation of active compound, 1 part by weight of active compound was mixed with the stated amounts of solvent and emulsifier and made up with water to the desired concentration.

Groups of 50 cress seeds were placed on a stiff filter paper cut to a rectangular shape, which was impregnated with an 0.02% strength solution of the particular preparation of active compound. The seeds adhered so firmly to the moist filter paper that they did not fall off even when the paper was stood upright. The moist filter paper carrying the seeds was placed vertically in a beaker (diameter about 7 cm) which contained 25 ml

Table A

Suppression of side-shoot growth in tobacco

| Active compound | Concentration (in %) | Damage | Total weight of the shoots of 2 plants (in g) |
|---|---|---|---|
| Water (control) | 0 | 0 | 45.2 |
| 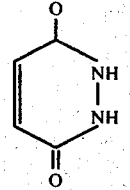 (known) | 0.05 | 0 | 1.2 |
| 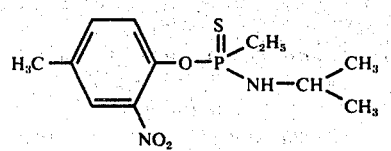 (1) | 0.05 | 0 | 0 |

EXAMPLE B

Influence on growth/cress seedlings
Solvent: 10 parts by weight of methanol
Emulsifier: 2 parts by weight of polyethylene-sorbitan monolaurate of an 0.02% strength solution of active compound. The beaker was covered with a glass disc. After 5 days, the experiment was evaluated.

The active compounds, active compound concentrations and results can be seen from the table which follows:

Table B

Influence on growth / cress seedlings

| Active compound | Concentration (in %) | Inhibition of growth | Thickened hypocotyl |
|---|---|---|---|
| Water (control) | 0 | 0 | 0 |
| 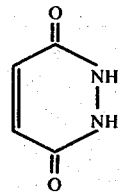 (known) | 0.02 | + | 0 |
| 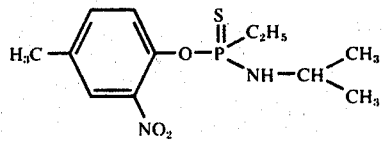 | 0.02 | ++ | + |

Table B-continued

| Active compound | Influence on growth / cress seedlings Concentration (in %) | Inhibition of growth | Thickened hypocotyl |
|---|---|---|---|
| 1) | | | |

In the table the symbols denote the following:
− = normal development
· = distinct effect
+ = very strong effect
('strong inhibition of growth and, in some cases, a thickening of the hypocotyl can be observed in the plants treated with the active compounds, as compared to the control plants.

EXAMPLE 1

Preparation of O:(2-Nitro-4-methylphenyl)-N-isopropylethane-thionophosphonamide.

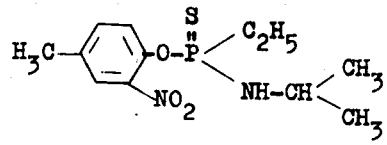 (1)

27.7 g of anhydrous potassium carbonate were added to a solution of 30.6 g (0.02 mole) of 2-nitro-4-methylphenol in 500 ml of acetonitrile. The mixture was stirred for 30 minutes at a temperature of 50 – 55°C. Thereafter, 37.1 g (0.2 mole) of N-isopropyl-ethanethionophosphonamide chloride were added dropwise to the reaction mixture at 50° – 55°C. In order to achieve as complete a reaction as possible, the mixture was next stirred for a further hour at 55° – 60°C and then for a further 2 hours at a temperature of 65° – 70°C. The acetonitrile was then distilled from the reaction mixture and the residue which remained was taken up in 100 ml of benzene. The resulting solution was successively washed with an 0.2% strength potassium hydroxide solution and with water. After subsequent drying of the organic phase over sodium sulphate, the solution was concentrated by distilling off the solvent and the residue which remained was subjected to a fractional vacuum distillation. In this way, 49 g (81% of theory) of O-(2-nitro-4-methylphenyl)-N-isopropylethane-thionophosphonamide of boiling point 50° – 60°C/0.1 mm Hg were obtained. After recrystallization, the product was obtained in the form of pale yellow crystals of melting point 64°C.

The starting material was prepared as follows:

$$\underset{\underset{NH-CH(CH_3)_2}{|}}{\overset{\overset{S}{\|}}{H_5C_2-P-Cl}}$$

59.1 g (1 mole of isopropylamine were added dropwise, at a temperature of 0°C, to a solution of 81.5 g (0.5 mole) of ethanethionophosphonyl dichloride in 300 ml toluene. After completion of the addition, the mixture was next stirred for a further hour at 0°C and then for 3 hours at room temperature. The reaction product was isolated by filtering off the isopropylamine hydrochloride which had precipitated and by concentrating the resulting solution under reduced pressure. The residue which remained was subjected to a fractional vacuum distillation. This gave 55 g (59% of theory) of N-isopropyl-ethanethionophosphonamide chloride of boiling point 90° – 95°C/0.5 mm Hg.

It will be understood that the foregoing specification and examples are illustrative and not limitative of the present invention in that many other embodiments of the invention will suggest themselves to those skilled in the art.

What is claimed is:

1. Method of suppressing the growth of side shoots in tobacco plants which method comprises applying to the tobacco plants or their habitat an effective amount of O-(2-nitro-4-methylphenyl)-N-isopropylethane-thionophosphonamide of the formula

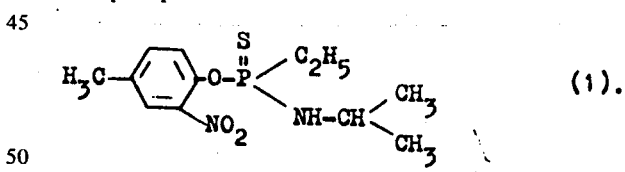 (1).

* * * * *